United States Patent
Ulmer

(10) Patent No.: US 10,330,586 B2
(45) Date of Patent: Jun. 25, 2019

(54) CORROSION MONITOR

(71) Applicant: HONEYWELL INTERNATIONAL INC., Morris Plains, NJ (US)

(72) Inventor: Rick Ulmer, Olathe, KS (US)

(73) Assignee: HONEYWELL INTERNATIONAL INC., Morris Plains, NJ (US)

(*) Notice: Subject to any disclaimer, the term of this patent is extended or adjusted under 35 U.S.C. 154(b) by 342 days.

(21) Appl. No.: 15/215,269

(22) Filed: Jul. 20, 2016

(65) Prior Publication Data

US 2018/0024042 A1     Jan. 25, 2018

(51) Int. Cl.
| | |
|---|---|
| *G01R 27/08* | (2006.01) |
| *G01N 17/00* | (2006.01) |
| *G01N 17/04* | (2006.01) |
| *G01N 27/04* | (2006.01) |

(52) U.S. Cl.
CPC ........... *G01N 17/006* (2013.01); *G01N 17/04* (2013.01); *G01N 27/041* (2013.01); *G01R 27/08* (2013.01)

(58) Field of Classification Search
CPC .. G01N 17/2006; G01N 17/04; G01N 27/041; G01R 27/08
See application file for complete search history.

(56) References Cited

U.S. PATENT DOCUMENTS

| | | | |
|---|---|---|---|
| 5,446,369 A | * | 8/1995 | Byrne .................... G01N 17/00 204/404 |
| 6,690,182 B2 | * | 2/2004 | Kelly ................... G01N 17/006 324/700 |
| 6,919,729 B2 | * | 7/2005 | Tiefnig .................. G01N 17/00 324/700 |

(Continued)

FOREIGN PATENT DOCUMENTS

| | | | | |
|---|---|---|---|---|
| EP | 3273221 A1 | * | 1/2018 | ........... G01N 17/006 |
| GB | 2470225 A | * | 11/2010 | ............. G01N 17/04 |

(Continued)

OTHER PUBLICATIONS

Extended EP Search Report for Application No. 17178546.2-1559 dated Oct. 10, 2017.

(Continued)

*Primary Examiner* — Patrick Assouad
*Assistant Examiner* — Sean Curtis
(74) *Attorney, Agent, or Firm* — Lorenz & Kopf, LLP

(57) ABSTRACT

A corrosion detection system and a method for operating a corrosion detection system are provided. The system, may include, but is not limited to, a PCB, a corrosion sensor, a first, second, third and fourth standoff coupled between the PCB and a chassis, a constant current circuit coupled to the first standoff, a first trace coupled between the third standoff and a first input of the corrosion sensor, and a second trace coupled between the fourth standoff and a second input of the corrosion sensor, wherein the corrosion sensor is configured to output a signal proportional to the resistance of the chassis based upon a voltage induced at the first input and the second input, and a processor configured to receive the signal proportional to the resistance of the chassis and determine a corrosion level of the chassis by comparing the signal to reference data stored in memory.

18 Claims, 4 Drawing Sheets

(56) References Cited

U.S. PATENT DOCUMENTS

| | | | | |
|---|---|---|---|---|
| 7,313,947 | B2* | 1/2008 | Harris | G01N 17/006 324/71.2 |
| 7,913,570 | B2* | 3/2011 | Forsyth | G01N 17/04 73/779 |
| 7,915,901 | B2* | 3/2011 | Bell | G01N 17/04 324/700 |
| 7,986,218 | B2* | 7/2011 | Watters | G01D 5/48 324/693 |
| 8,085,165 | B2* | 12/2011 | Wavering | H04Q 9/00 340/870.02 |
| 9,291,543 | B1* | 3/2016 | Robinson | G01N 17/006 |
| 9,685,201 | B2* | 6/2017 | Iben | G01R 33/098 |
| 2004/0130340 | A1* | 7/2004 | Tiefnig | G01N 17/00 324/700 |
| 2006/0002815 | A1* | 1/2006 | Harris | G01N 17/006 422/53 |
| 2006/0125480 | A1* | 6/2006 | Srinivasan | G01N 17/02 324/376 |
| 2006/0162431 | A1* | 7/2006 | Harris | G01N 17/006 73/86 |
| 2007/0163892 | A1* | 7/2007 | Haridas | G01N 17/04 205/776.5 |
| 2008/0204275 | A1* | 8/2008 | Wavering | G01N 17/04 340/870.16 |
| 2009/0085585 | A1* | 4/2009 | Lu | G01N 17/02 324/700 |
| 2009/0195260 | A1* | 8/2009 | Bell | G01N 17/04 324/700 |
| 2012/0007579 | A1* | 1/2012 | Apblett | G01N 17/04 324/71.1 |
| 2014/0152449 | A1* | 6/2014 | Klein | H05K 1/0268 340/662 |
| 2015/0377814 | A1* | 12/2015 | Schindelholz | G01N 27/026 324/693 |
| 2016/0091413 | A1* | 3/2016 | Kim | G01N 17/02 204/404 |
| 2016/0139029 | A1* | 5/2016 | Belsom | G01N 17/04 422/53 |
| 2017/0011777 | A1* | 1/2017 | Iben | G01R 33/098 |
| 2018/0024042 | A1* | 1/2018 | Ulmer | G01N 17/006 324/700 |

FOREIGN PATENT DOCUMENTS

| | | | | |
|---|---|---|---|---|
| GB | | 2470225 A | * 11/2010 | G01N 17/00 |
| GB | | 2470225 A | 11/2010 | |
| WO | | 2004031739 A2 | 4/2004 | |
| WO | WO-2017175507 A1 | * 10/2017 | | G01N 17/00 |

OTHER PUBLICATIONS

Walter Leon-Salas, Sirsha Kanneganti and Ceki Halmen, "Development of a Smart RFID-Based Corrosion Sensor", IEEE, Mar. 2011.

Khalada Perveen, et al., "Corrosion Potential Sensor for Remote Monitoring of Civil Structure Based on Printed Circuit Board Sensor", IEEE Transactions on Instrumentation and Measurement, vol. 63, No. 10, Oct. 2014, pp. 2422-2434.

EP Examination Report for Application No. 17178546.2-1559 dated Mar. 20, 2018.

* cited by examiner

CORROSION MONITOR

TECHNICAL FIELD

The present disclosure generally relates to an electrical device, and more particularly relates a corrosion monitor for monitoring corrosion of a chassis.

BACKGROUND

Corrosion is a natural process which converts a refined metal to a more stable form, such as its oxide, hydroxide or sulfide forms. Corrosion generally occurs when a metal is exposed to oxygen. However, the speed at which a metal experiences corrosion can be affected by temperature, moisture (i.e., humidity), salt and a variety of other factors.

Corrosion to a metal damages the structural integrity of the metal. Corrosion to a metal may also indicate that the metal was exposed to moisture which can also negatively affect electronic equipment housed within or near the metal. Accordingly, a system and method for detecting corrosion is desirable.

BRIEF SUMMARY

In one embodiment, for example, a corrosion detection system for detecting corrosion on a chassis of a device is provided. The system may include, but is not limited to, a memory configured to store reference data, a corrosion monitor including, but not limited to, a printed circuit board, a corrosion sensor coupled to the printed circuit board, the corrosion sensor comprising a first input and a second input, the corrosion sensor configured to output a signal proportional to a resistance of the chassis of the device, a first standoff coupled between the printed circuit board and the chassis of the device, a second standoff coupled between the printed circuit board and the chassis of the device, a third standoff coupled between the printed circuit board and the chassis of the device, a fourth standoff coupled between the printed circuit board and the chassis of the device, a constant current circuit coupled to the first standoff and configured to output a constant current, a first trace coupled between the third standoff and the first input of the corrosion sensor, and a second trace coupled between the fourth standoff and the second input of the corrosion sensor, wherein the corrosion sensor is configured to output the signal proportional to the resistance of the chassis of the device based upon a voltage induced by the constant current circuit at the first input and the second input, and a processor communicatively coupled to the memory and the corrosion monitor, the processor configured to receive the signal proportional to the resistance of the chassis of the device from the corrosion monitor and determine a corrosion level of the chassis of the device by comparing the signal proportional to the resistance of the chassis from the corrosion monitor to the reference data stored in the memory.

In another embodiment, for example, a method for detecting corrosion on a chassis of a device is provided. The method may include, but is not limited to, receiving, by a constant current source mounted on a printed circuit board, a power supply, outputting, by the constant current source, a substantially constant current to a first standoff, the first standoff separating the printed circuit board from the chassis, receiving, by a corrosion sensor mounted on the printed circuit board, a first input voltage from a second standoff, the second standoff separating the printed circuit board from the chassis, receiving, by the corrosion sensor, a second input voltage from a third standoff, the third standoff separating the printed circuit board from the chassis, outputting, by the corrosion sensor, a signal proportional to a resistance of the chassis based upon the first input voltage and the second input voltage to a processor mounted on the printed circuit board, and determining, by the processor, a corrosion level of the chassis by comparing the signal proportional to the resistance of the chassis to reference data stored in a memory communicatively coupled to the processor.

In yet another embodiment, for example, a corrosion detection system for an electronics assembly is provided. The system may include, but is not limited to, a metal chassis configured to support an electronics device, a corrosion monitor including an insulated substrate, a plurality of standoffs extending between the insulated substrate and the metal chassis, a constant current circuit supported on the insulated substrate and electrically coupled to a first standoff for outputting a constant current to the metal chassis, a corrosion sensor supported on the insulated substrate and having a first input electrically coupled to a second standoff, a second input electrically coupled to a third standoff, and an output configured to output a signal proportional to a resistance of the metal chassis based upon a voltage induced by the constant current circuit at the first input and the second input, and a processor in communication with the corrosion monitor and configured to receive the signal proportional to the resistance of the chassis of the device from the corrosion monitor, determine a corrosion level of the chassis of the device by comparing the signal proportional to the resistance of the chassis from the corrosion monitor to the reference data stored in a memory associated with the processor, and output a signal based on the corrosion level.

BRIEF DESCRIPTION OF THE DRAWINGS

The detailed description will hereinafter be described in conjunction with the following drawing figures, wherein like numerals denote like elements, and wherein.

DETAILED DESCRIPTION

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

Figure 1:
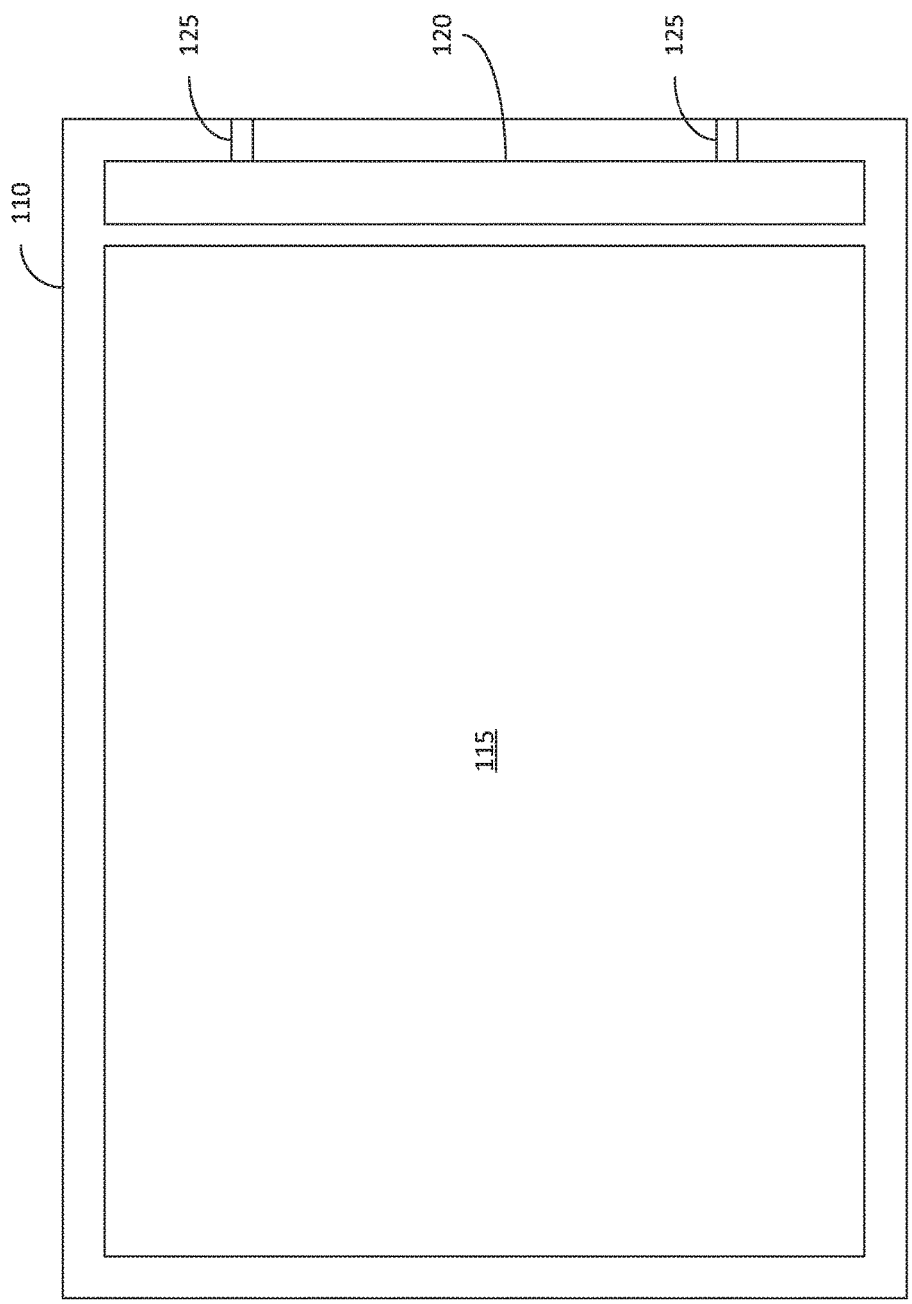
FIG. 1 is a block diagram of a system for monitoring corrosion in a chassis, in accordance with an embodiment.

FIG. 1 is a block diagram of a system 100 for monitoring corrosion in a chassis 110, in accordance with an embodiment. In one embodiment, for example, the chassis 110 may hold electronic equipment 115 in, for example, an aircraft or any other vehicle. In an aircraft, for example, the electronic equipment 115 housed within the chassis 110 may be a flight management system (FMS), an automatic direction finder (ADF), a navigation system, a communication system, or other equipment within the aircraft cockpit. When the chassis 110, and thus the electronic equipment 115 housed therein, is exposed to moisture, corrosion of the chassis 110 and of the electronic equipment 115 held therein can occur. The system 100 monitors for corrosion of the chassis 110 such that any corrosion of the chassis 110 and therefore possible damage of the electronic equipment 115 therein, can be detected and corrected before any problem can occur. In other embodiments, for example, the system 100 could monitor for corrosion in other areas prone to corrosion, such as fuel pumps, mounting brackets, gas tanks, and the like. In these embodiments, the system 100 could be mounted directly to the element which is prone to corrosion. However, for sake of simplicity, the system 100 will hereinafter be discussed in the context of a chassis 110 housing electronic equipment.

The system 100 includes a corrosion monitor 120. The corrosion monitor 120 monitors the chassis 110 for corrosion. The corrosion monitor 120 is electrically connected to the chassis 110 through multiple standoffs 125. As discussed in further detail below, the corrosion monitor 120 outputs a current to the chassis 110 through one of the standoffs 125 and determines a level of corrosion of the chassis 110 by monitoring a voltage induced by the current on the other standoffs 125.

Figure 2:
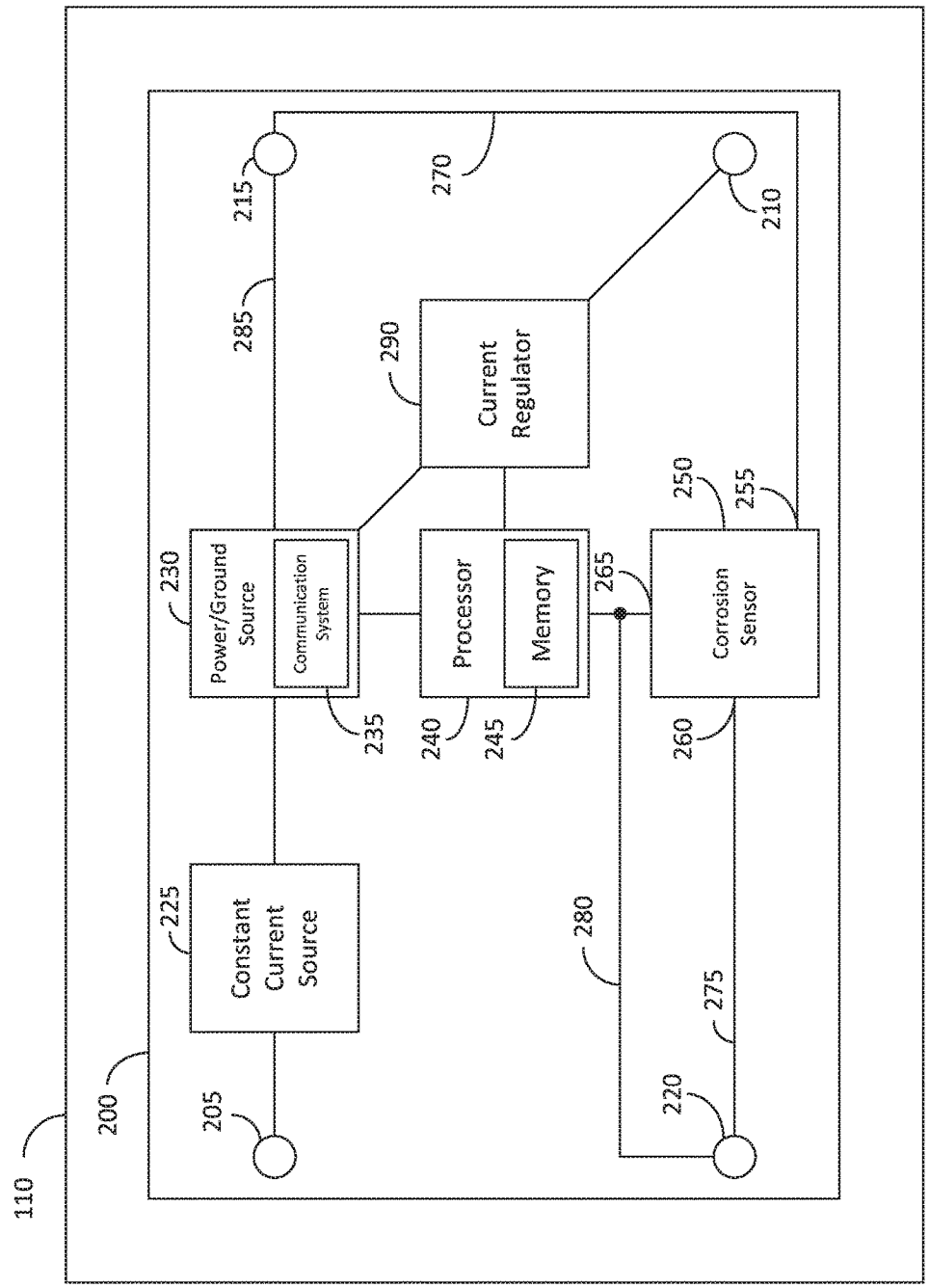
FIG. 2 is a block diagram of the corrosion monitor, in accordance with an embodiment.

FIG. 2 is a block diagram of the corrosion monitor 120, in accordance with an embodiment. The corrosion monitor 120 includes a printed circuit board 200. The printed circuit board 200 may be mounted within an interior of the chassis 110 or on the exterior of the chassis 110. The corrosion monitor 120 includes standoffs 125, herein after referred to as standoffs 205, 210, 215 and 220 which separate the printed circuit board 200 from the chassis 110. The standoffs 205-220 may be formed from any conductive material and may be of any length which effectively separates the printed circuit board 200 from having direct contact with the chassis 110. The standoffs 205-220 may be connected to the chassis and the printed circuit board 200 by screws, bolts, solder, welds, or the like, or any combination thereof.

The corrosion monitoring circuit includes a constant current source 225. The constant current source 225 outputs a current of a predetermined amplitude and which is substantially constant (i.e., has a variation less than around, for example, 1 milliamp (ma)) to one of the standoffs 205-220, in the example illustrated in FIG. 2, standoff 205. In one embodiment, for example, the constant current source 225 may output a one-hundred picoamp current to the standoff 205. However, the magnitude of the current output by the constant current source 225 could be any predetermined value. The current provided to the standoff 205 by the constant current source 225 is passed to the chassis 110 via the electrical connection there between. As discussed in further detail below, the current provided to the chassis 110 is used to determine the amount of corrosion of the chassis 110.

The corrosion monitor 120 further includes a power/ground source 230. The power/ground source provides a power to the constant current source 225 so the constant current source 225 can provide the current to the chassis 110 as discussed above. The power/ground source 230 also provides a ground reference for the corrosion monitor 120, which is discussed in further detail below.

In one embodiment, for example, the power/ground source 230 may be a near filed communication (NFC) tag or a radio frequency identification (RFID) tag. In this embodiment, the power/ground source 230 would itself receive power from an active NFC-enabled device or an active RFID-enabled device (not illustrated) when the respective device is within range of the respective tag. The NFC-enabled device or RFID-enabled device could be, for example, a cellular phone, a tablet, or any other NFC or RFID communication system. In this embodiment, the power/ground source 230 may also function as a communication system 235. The NFC tag or RFID tag could transmit information, such as the corrosion level of the chassis 110, to the NFC- or RFID-enabled device when the respective device is within range. One benefit of this embodiment, for example, is that the NFC tag or an RFID tag can provide a combined power source and communication system, rather than requiring separate systems. Another benefit of this embodiment is that the corrosion monitor 120 can be simply activated on demand when the NFC-enabled device or RFID-enabled device is brought into close approximation to the NFC tag or an RFID tag.

In another embodiment, for example, the power/ground source 230 may be part of the electronic device 115 housed within the chassis 110. In another embodiment, for example, the power/ground source 230 may be dedicated to the system 100, and may be, for example, a battery, supercapacitor, or the like. In these embodiments, the communication system 235 would be separate from the power/ground source 230. The communication system 235 may be, for example, a Wi-Fi communication system, a Bluetooth communication system, a ZigBee communication system, a cellular communication system, any wired communication system, or the like, or any combination thereof.

The corrosion monitor 120 may further include a processor 240. The processor 240 may be, for example, an ARM logic device. One benefit of utilizing an ARM logic device is that it requires little power to operate. Accordingly, when the power/ground source 230 is a NFC tag or RFID tag, the respective tag can supply enough power to enable operation of the ARM log device. In other embodiments, for example, the processor may be a central processing unit (CPU), a microcontroller, an application specific integrated circuit (ASIC), a field programmable gate array (FPGA), or any other logic device or combination thereof.

The corrosion monitor 120 may further include a memory 245. The memory 245 may be any non-volatile memory. In one embodiment, for example, the memory 245 may be incorporated within the processor 240, as illustrated in FIG. 2. However, in other embodiments, the memory 245 may be separate from the processor 240 and may be, for example, a stand-alone memory unit or may be a memory shared with the electronic device 115 housed within the chassis 110. The memory 245 may be utilized to store results of one or more corrosion tests performed by the corrosion monitor 120 as well as reference data utilized to test for corrosion, as discussed in further detail below.

The corrosion monitor 120 further includes a corrosion sensor 250. The corrosion sensor 250 includes two inputs 255 and 260 and an output 265. Input 255 is coupled to standoff 215 through PCB trace 270. Input 260 is coupled to standoff 220 through PCB trace 275. The output 265 of the corrosion sensor 250 is coupled to the standoff 220 through PCB trace 280 and provides feedback for the corrosion sensor 250. In one embodiment, for example, the corrosion sensor 250 may include an operational amplifier configured to compare the voltage at the first input 255 to the voltage at the second input 260. However, the corrosion sensor 250 could be achieved using a variety of components or any other comparator circuit.

The corrosion sensor 250 receives an input voltage at input 255 and an input voltage at input 260. The input voltages are affected by any corrosion of the chassis 110, as discussed in further detail with reference to FIG. 3. The output of the corrosion sensor is proportional to a corrosion level of the chassis 110, as discussed in further detail below.

Figure 3:
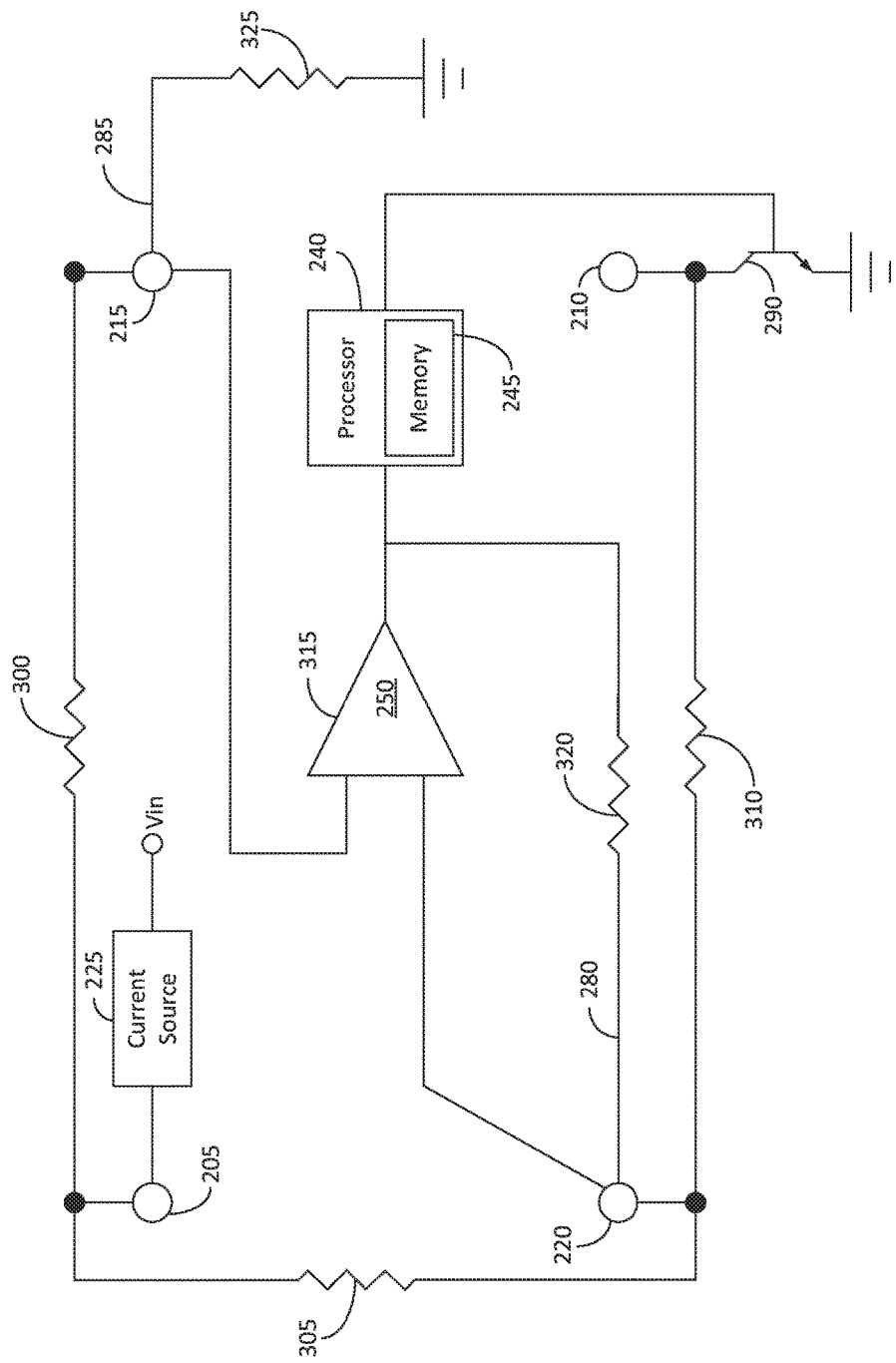
FIG. 3 illustrates a circuit equivalent of the corrosion monitor illustrated in FIG. 2.

FIG. 3 illustrates a circuit equivalent of the corrosion monitor 120 illustrated in FIG. 2. The current source 225 outputs a current to the chassis 110 through the standoff 205. The current will pass through the chassis 110 and return to the corrosion monitor 120 through standoffs 210, 215 and 220. Any corrosion of the chassis 110 changes the resistance the chassis 110, which in turn will affect a measurable voltage induced by the current source at the standoffs 210, 215 and 220 to indicate a corrosion level of the chassis 110. In FIG. 3, the resistance of the chassis 110 is represented by resistors 300, 305 and 310. Resistor 300 represents the resistance of the chassis 110 between standoffs 205 and 215. Resistor 305 represents the resistance of the chassis 110 between standoffs 205 and 220. Resistor 310 represents the resistance of the chassis 110 between standoffs 210 and 220.

As seen in FIGS. 2 and 3, the corrosion sensor 250, represented in FIG. 3 as op amp 315, receives a voltage from standoff 215 and standoff 220. As the current output by the current source 225 is fixed, the voltage at the standoffs 215 and 220 is proportional to the known constant current and the variable resistance, due to corrosion, of the chassis 110. Because the corrosion monitor 120 is coupled to the chassis at four points (i.e., at standoffs 205-220), the voltages at standoffs 215 and 220 takes into account any corrosion of the chassis over a wider area than other corrosion monitors which only utilize two connection points, thereby allowing the corrosion sensor 250 to more accurately measure the corrosion level of the chassis 110.

The PCB trace 280 connected between the output of the op amp 315 and standoff 220 has a built-in resistance, represented in FIG. 3 as a resistor 320. In one embodiment, for example, the resistance of PCB trace 280 may be, for example, 10 milliohms. However the resistance of PCB trace 280 may vary depending on length, width, and thickness of trace. The resistance of PCB trace 280 provides feedback to the corrosion sensor 250. A small increase in series resistance of the PCB trace 280 attached to the standoff 220 would affect feedback and gain of the circuit and indicate corrosion.

The PCB trace 285 connected between standoff 215 and the ground reference of the power/ground source 230, also has a built-in resistance, represented in FIG. 3 as a resistor 325. In one embodiment, for example, the resistance of PCB trace 285 may be, for example, 10 milliohms. However the resistance of PCB trace 285 may vary.

The output of the corrosion sensor 250 is based upon the voltages at the standoffs 215 and 220 induced by the current source 225. The corrosion sensor 250 may, for example, compare the voltages at the standoffs 215 and 220. Because the constant current source 225 is outputting a constant current, the voltages at standoffs 215 and 220 should be substantially similar when no corrosion is present on the chassis 110, but will diverge when corrosion is present as corrosion changes the resistance of the chassis 110.

The output of the corrosion sensor 250 is transmitted to the processor 240. The processor 240 compares the received output of the corrosion sensor 250 to a reference value stored in the memory 245. In one embodiment, for example, the reference value stored in the memory may be a voltage representative of the corrosion level of the chassis. However, in other embodiments, the reference value(s) may be stored as resistances. In this embodiment, for example, the processor 240 would convert the voltage proportional to the resistance of the chassis received from the corrosion sensor 250 by dividing the voltage proportional to the resistance of the chassis by the known amplitude of the constant current source 225.

In one embodiment, for example, the corrosion monitor 120 may further include a current regulator 290 which regulates the current of the constant current source 225. In one embodiment, as seen in FIG. 3, the current regulator may simply be a transistor. However, a variety of components could be used to form the current regulator 290. When the PCB resistance (such as 310) increases, the current output by the constant current source 225 would normally decrease. However, as the change is sensed by the corrosion sensor 250 and transmitted to the processor 240, the processor 240 can drive the current regulator (e.g., increase a voltage to a gate of the transistor) to increase the current output by the constant current source 225 to maintain the predetermined current output and causing a higher voltage drop at the inputs to the corrosion sensor 250. In other words, the current regulator 290 provides feedback to help provide some hysteresis, but is not necessarily needed in all embodiments.

Figure 4:
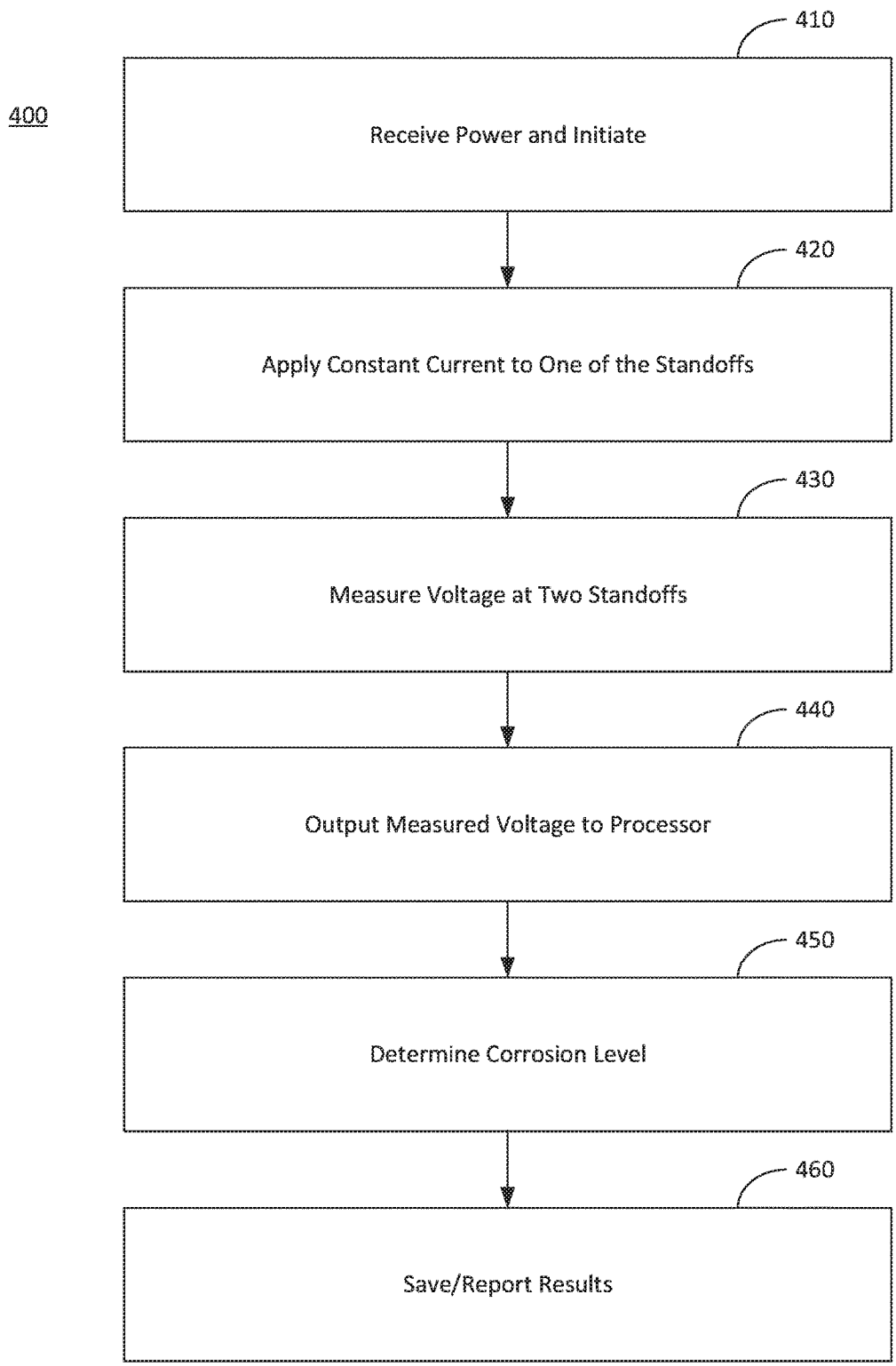
FIG. 4 is a flow chart illustrating an exemplary method for operating the system, in accordance with an embodiment.

FIG. 4 is a flow chart illustrating an exemplary method 400 for operating the system 100, in accordance with an embodiment. The method 400 begins when the system 100 receives power and initiates. (Step 410). In one embodiment, as discussed above, the power/ground source 230 may be an RFID tag or a NFC tag. Accordingly, in this embodiment, the system 100 receives power when a corresponding RFID- or NFC-enabled device is within range of the RFID tag or NFC tag, respectively. When the RFID- or NFC-enabled device is within range of the respective RFID tag or NFC tag, the RFID tag or NFC tag receive power from the RFID- or NFC-enabled device, thus enabling the RFID tag or NFC tag to provide power to the constant current source 225, the processor 240 and any other components of the corrosion monitor 120 which require power to operate. In this embodiment, the corrosion monitor 120 may begin operation (i.e., initiate the corrosion test) immediately upon receiving power. However, in other embodiments, the corrosion test may be initiated through communication between the RFID- or NFC-enabled device and the RFID or NFC tag, or through another interface, such as a button (not illustrated) on the chassis 110, or the like. In other embodiments where the power/ground source 230 is provided by the electronic device 115 or another power/ground source, the corrosion test may be initiated through an interface of the electronic device, through a button on the chassis 110, or the like.

When the corrosion monitor 120 is initiated, the constant current source 225 outputs a constant current to just one of the standoffs 205-220, standoff 205 as illustrated in FIGS. 2 and 3. (Step 420). As discussed above, the current applied to the standoff 205 induces a voltage on standoffs 215 and 220 which is proportional to corrosion of the chassis 110.

After the constant current source 225 outputs the constant current to the standoff 205, the corrosion sensor 250 measures a voltage induced by the current on the standoffs 215 and 220. (Step 430). In one embodiment, for example, the corrosion sensor 250 may output a difference between the voltage induced by the current on the standoffs 215 and 220. Any difference between the voltage induced by the current on the standoffs 215 and 220 indicates the presence of corrosion on the chassis 110. The corrosion sensor 250 then outputs the voltage to the processor 240. (Step 440)

The processor 240 then determines a corrosion level of the chassis 110. (Step 450). In one embodiment, for example, the processor 240 may compare the received voltage with reference data stored in the memory 245. The reference data may include one or more values based upon a baseline resistance measurement of the chassis 110. For example, during installation of the chassis 110, or as part of the manufacturing process, a baseline measurement of the resistance of the chassis 110 may be made. The baseline resistance of the chassis 110 is measured as there could be manufacturing variation and/or, the corrosion monitor 120 could be added to the chassis 110 by someone other than the manufacturer. The value(s) of the reference data may correspond to one or more corrosion levels of the chassis 110. For example, a first reference value may correspond to the baseline resistance plus a first predetermined increase based upon a linear relationship (i.e., corrosion linearly increases the resistance of the chassis 110 as the corrosion increases) to the reference value, which represents a tolerable amount of corrosion of the chassis. The processor 240 may determine that the corrosion level of the chassis is at an acceptable level when the received voltage is less than the first reference value or that the corrosion level of the chassis is at an unacceptable level when the received voltage is greater than the first reference value. However, any number of corrosion levels could be established. For example, a voltage between the first reference value and a second reference value may correspond to a warning level and voltages greater than the second reference value may correspond to the unacceptable corrosion level.

The processor 240 may then save and/or report the determined corrosion level. (Step 460). In one embodiment, for example, the processor 240 may save the voltage output by the corrosion sensor 250 in the memory 245 to generate a history of the corrosion level of the chassis 110. In another embodiment, for example, the processor 240 may merely save the last measurement such that an increase of corrosion between tests can be determined. The determined corrosion level and/or any historic data may also be transmitted to a receiving device (not illustrated). For example, when the corrosion monitor includes an RFID or NFC tag, the processor 240 may direct the RFID or NFC tag to transmit the data to an RFID- or NFC-enabled device. In other embodiments, other communication systems 235 may be used to transmit the determined corrosion level and/or any historic data to a receiving device. In another embodiment, for example, the receiving device may be part of the electronic device 115, such as a video screen, warning light or the like which can visualize or otherwise indicate the corrosion level of the chassis to a maintenance technician or other user of the electronic device 115. Any combination of these methods may be used to report the corrosion level and/or any historic data saved in the memory 245.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A corrosion detection system for detecting corrosion on a chassis of a device, comprising:
   a memory configured to store reference data;
   a corrosion monitor comprising:
      a printed circuit board;
      a corrosion sensor coupled to the printed circuit board, the corrosion sensor comprising a first input and a second input, the corrosion sensor configured to output a signal proportional to a resistance of the chassis of the device;
      a first standoff coupled between the printed circuit board and the chassis of the device;
      a second standoff coupled between the printed circuit board and the chassis of the device;
      a third standoff coupled between the printed circuit board and the chassis of the device;
      a fourth standoff coupled between the printed circuit board and the chassis of the device;
      a constant current circuit coupled to the first standoff and configured to output a constant current;
      a first trace coupled between the third standoff and the first input of the corrosion sensor; and
      a second trace coupled between the fourth standoff and the second input of the corrosion sensor,
      wherein the corrosion sensor is configured to output the signal proportional to the resistance of the chassis of the device based upon a voltage induced by the constant current circuit at the first input and the second input; and
   a processor communicatively coupled to the memory and the corrosion monitor, the processor configured to receive the signal proportional to the resistance of the chassis of the device from the corrosion monitor and determine a corrosion level of the chassis of the device by comparing the signal proportional to the resistance of the chassis from the corrosion monitor to the reference data stored in the memory; and
   a current regulator coupled between the second standoff and the processor.

2. The corrosion detection system of claim 1, further comprising:
   a passive near field communication circuit galvanically coupled to the memory, the corrosion monitor and the processor, the passive near field communication circuit configured to power the memory, the corrosion monitor and the processor when the passive near field communication circuit is exposed to a radio frequency field by an active near field communication system.

3. The corrosion detection system of claim 2, wherein the passive near field communication circuit is further configured to transmit the determined corrosion level to the active near field communication system.

4. The corrosion detection system of claim 1, further comprising:
   a radio frequency identification communication circuit galvanically coupled to the memory, the corrosion monitor and the processor, the radio frequency identification communication circuit configured to power the memory, the corrosion monitor and the processor when the radio frequency identification communication circuit is exposed to a radio frequency field by an active radio frequency identification communication system.

5. The corrosion detection system of claim 4, wherein the radio frequency identification communication circuit is further configured to transmit the determined corrosion level to the active near field communication system.

6. The corrosion detection system of claim 1, wherein the reference data is a reference voltage.

7. A method for detecting corrosion on a chassis of a device, comprising:
   receiving, by a constant current source mounted on a printed circuit board, a power supply;
   outputting, by the constant current source, a substantially constant current to a first standoff, the first standoff separating a first corner of the printed circuit board from the chassis;
   receiving, by a corrosion sensor mounted on the printed circuit board, a first input voltage from a second standoff, the second standoff separating a second corner of the printed circuit board from the chassis;
   receiving, by the corrosion sensor, a second input voltage from a third standoff, the third standoff separating a third corner of the printed circuit board from the chassis;
   outputting, by the corrosion sensor, a signal proportional to a resistance of the chassis based upon the first input voltage and the second input voltage to a processor mounted on the printed circuit board; and
   determining, by the processor, a corrosion level of the chassis by comparing the signal proportional to the resistance of the chassis to reference data stored in a memory communicatively coupled to the processor.

8. The method of claim 7, further comprising transmitting, by a passive near field communication circuit, the power supply to the constant current source when the passive near field communication circuit is exposed to a radio frequency field by an active near field communication system.

9. The method of claim 8, further comprising transmitting, by the passive near field communication circuit, the determined corrosion level to the active near field communication system.

10. The method of claim 7, further comprising transmitting, by a radio frequency identification communication circuit, the power supply to the constant current source when the radio frequency identification communication circuit is exposed to a radio frequency field by an active radio frequency identification communication system.

11. The method of claim 10, further comprising transmitting, by the radio frequency identification communication circuit, the determined corrosion level to the active radio frequency identification communication system.

12. The method of claim 7, wherein the reference data is a reference voltage.

13. A corrosion detection system for an electronics assembly comprising:
   a metal chassis configured to support an electronics device;
   a corrosion monitor including:
      an insulated substrate;
      a plurality of standoffs extending between the insulated substrate and the metal chassis;
      a constant current circuit supported on the insulated substrate and electrically coupled to a first standoff for outputting a constant current to the metal chassis;
      a corrosion sensor supported on the insulated substrate and having a first input electrically coupled to a second standoff, a second input electrically coupled to a third standoff, and an output configured to output a signal proportional to a resistance of the metal chassis based upon a voltage induced by the constant current circuit at the first input and the second input; and
   a processor in communication with the corrosion monitor and configured to receive the signal proportional to the resistance of the chassis of the device from the corrosion monitor, determine a corrosion level of the chassis of the device by comparing the signal proportional to the resistance of the chassis from the corrosion monitor to the reference data stored in a memory associated with the processor, and output a signal based on the corrosion level; and
   a power/ground source galvanically coupled to the corrosion monitor and the processor for selectively powering the corrosion monitor and the processor when a corrosion detection query is initiated.

14. The corrosion detection system of claim 13 further comprising a current regulator operably coupled between the power/ground source and at least one of the processor and a fourth standoff.

15. The corrosion detection system of claim 13 wherein the power/ground source further comprises a near field circuit configured to power the corrosion monitor and the processor when the near field circuit is exposed to a query signal from a near field activation device.

16. The corrosion detection system of claim 13 further comprising a receiving device in communication with the processor and configured to indicate the corrosion level based on the output signal.

17. The corrosion detection system of claim 13 wherein the reference data comprises a first reference value indicating an unacceptable corrosion level when the received voltage is greater than the first reference value.

18. The corrosion detection system of claim 17 wherein the reference data comprising a plurality of reference values, each reference value indicating a degree of corrosions level based on the received voltage.

* * * * *